(12) United States Patent
Struck et al.

(10) Patent No.: US 6,391,893 B1
(45) Date of Patent: *May 21, 2002

(54) PYRIDINE COMPOUNDS USE AND PREPARATION THEREOF

(75) Inventors: Robert F. Struck; Herbert M. Blatter; Anita Tiwari, all of Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/488,684

(22) Filed: Jan. 21, 2000

Related U.S. Application Data

(60) Provisional application No. 60/116,675, filed on Jan. 21, 1999.

(51) Int. Cl.[7] ..................... A61K 31/444; A61K 31/443; A61K 31/44; C07D 405/12; C07D 401/12; C07D 213/69
(52) U.S. Cl. ..................... 514/332; 514/333; 514/345; 514/348; 546/261; 546/283.4; 546/296
(58) Field of Search ................... 546/296, 261, 546/283.4; 514/348, 345, 332, 333

(56) References Cited

U.S. PATENT DOCUMENTS 4,717,726 A    1/1988   Tobol .................... 514/348

FOREIGN PATENT DOCUMENTS

WO    WO 97/46531    * 12/1997    .................. 514/348

OTHER PUBLICATIONS

L.G.Wade Jr. "Organic Chemistry". p. 415, Prentice Hall Publishers, 1987.*

* cited by examiner

*Primary Examiner*—Alan L. Rotman
(74) *Attorney, Agent, or Firm*—Connolly Bove Lodge & Hutz

(57) ABSTRACT

New pyridine compounds are provided along with their method of preparation. The compounds are useful as intermediates in preparing new anticancer agents. A few of the pyridine compounds are also useful for treating cancer.

18 Claims, No Drawings

PYRIDINE COMPOUNDS USE AND PREPARATION THEREOF

TECHNICAL FIELD

The present invention relates to certain novel pyridine compounds. The compounds of the present invention are especially useful for producing new acyl derivatives of 4-demethylpenclomedine (also referred to herein as DM PEN). The acyl derivatives, in turn, exhibit anticancer activity, and are the subject of U.S. patent application Ser. No. 60/116,675 filed Jan. 21, 1999 and entitled "Acyl Derivatives of 4-Demethylpenclomedine, Use and Preparation Thereof", the entire disclosure of which is incorporated herein by reference. Certain of the pyridine compounds of the present invention also exhibit anticancer activity. Accordingly, the present invention also relates to pharmaceutical compositions comprising those particular pyridine compounds, as well as a method of using them in treating cancer in a mammal. The present invention also relates to a method for producing the compounds of the present invention and to a method for producing the acyl derivatives of 4-demethylpenclomedine from the pyridine compounds of the present invention.

BACKGROUND OF INVENTION

Even though significant advances have occurred in treatment of cancer, it still remains a major health concern. It has been reported that cancer is the cause of death of up to one of every four Americans.

Included among the known chemotherapeutic drugs are carmustine, doxorubicin, methotrexate, TAXOL®, nitrogen mustard, procarbazine, and vinblastine, to name only a few. However, many chemotherapeutic drugs also produce undesirable side effects in the patient. For example, U.S. Pat. No. 4,717,726 reportedly discloses a compound suitable for inhibiting the growth of certain types of malignant neoplasms in mammals. See also Plowman et al., *Cancer Res.*, 49 (1989), 1909–1915. The disclosed compound, 3,5-dichloro-2,4-dimethoxy-6-(trichloromethyl)pyridine, also known as penclomedine, is not satisfactory as a chemotherapeutic, however, because it is known to produce certain undesirable side effects especially in the central nervous system.

For example, neurological and hematological toxicities of penclomedine have been reported in preclinical and early clinical studies. Dose related neurotoxicity, consisting of muscle tremors, incoordination, convulsions and reduced activity, has been observed in rats. Neurotoxicity appears to be related to peak plasma drug concentrations, as it developed during or immediately after infusion and could be ameliorated by decreasing the rate of drug administration. In dogs, severe emesis and seizures have been associated with plasma penclomedine levels above 30 μM. Neurotoxicity, consisting of dysmetria, ataxia, and vertigo, was also the principal dose limiting toxicity of penclomedine administered as a one hour infusion for 5 consecutive days in patients with advanced solid tumors. The presence of these toxicities, at much lower peak plasma concentrations compared to those reported in preclinical studies, may preclude the administration of higher doses of penclomedine and the achievement of concentrations associated with optimal antitumor activity. Berlin et al., *Proc. Amer. Assoc. Cancer Res.*, 36, 238 (1005); O'Reilly et al., *Proc. Amer. Soc. Clin. Oncol.*, 14, 471 (1995).

Some relevant background art can be found in O'Reilley et al., *Clinical Cancer Research*, 2 (March 1996), 541–548. This reference describes a study to assess the distribution of $^{14}$C-penclomedine in the tissues and tumors of tumor-bearing rats. The study found that the predominant radioactive species in the brain was penclomedine, which may explain the observed neurotoxicity of the drug.

More recently, 3,5-dichloro-2-methoxy-4-hydroxy-6-(trichloromethyl)pyridine or 4-demethylpenclomedine has been suggested as a compound for treating cancer. See WO 97/46531 to Hartman et al.

Notwithstanding the advances in cancer treatment that have been made, there still remains room for improved drugs that are effective in treating cancer, while at the same time exhibit reduced adverse side effects.

SUMMARY OF INVENTION

The present invention relates to new pyridine compounds that find especial utility as precursors for producing certain acyl derivatives of 4-demethylpenclomedine which, in turn, possess anticancer activity as will be discussed hereinbelow.

The compounds of the present invention are represented by the following formulae:

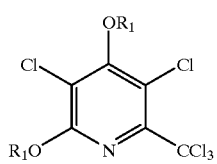

and

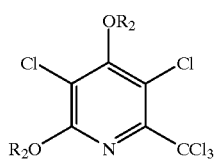

wherein
  each $R_1$ is independently an alkyl group provided that at least one $R_1$ is an alkyl group containing at least two carbon atoms; and
  each $R_2$ is independently H, acyl or an alkyl group having at least two carbon atoms or $R_2$ can be methyl in position 4 provided that $R_2$ is acyl in position 6.

The present invention also relates to a process for preparing compounds of formula I by reacting 3,4,5,6-tetrachloro-2-(trichloromethyl)pyridine with an alcohol in the presence of a base to produce the corresponding 3,5-dichloro-4,6-dialkoxy-2-(trichloromethyl)pyridine of formula I.

The compound according to formula II wherein both $R_2$ are H can be prepared by reacting the compound of formula I with a dealkylating agent such as anhydrous aluminum chloride to produce didemethylpenclomedine.

The compounds according to formula II wherein at least one of $R_2$ is acyl can be prepared by reacting didemethylpenclomedine with an acylating agent to form a corresponding acyl compound of formula II.

The acyl compound of formula II can then be reacted with an alkylating agent such as (trimethylsilyl)-diazomethane or diazomethane to produce the acyl derivatives of 4-demethylpenclomedine.

These novel acyl derivatives of 4-demethylpenclomedine compounds are represented by the formula:

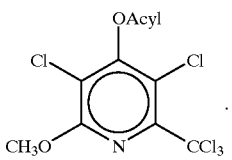

III

Pharmaceutically acceptable salts thereof can also be provided.

The present invention also relates to compounds represented by the formula

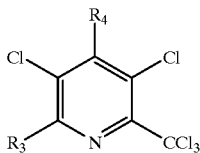

IV wherein one of $R_3$ or $R_4$ is Cl and the other of $R_3$ or $R_4$ is O-alkyl.

A further aspect of the present invention is concerned with producing compounds of formula IV. The compounds of formula IV can be produced by reacting 3,4,5,6-tetrachloro-2-(trichloromethyl)pyridine with an alcohol in the presence of a base and separating the desired compound from the reaction mixture.

Another aspect of the present invention relates to an alternative method for producing a compound of formula I above by reacting a compound of the formula IV

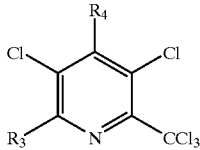

IV wherein one of $R_3$ or $R_4$ is Cl and the other of $R_3$ or $R_4$ is O-alkyl with an alcohol in the presence of a base.

In addition, compounds of formula I above can be produced by reacting a compound of the formula

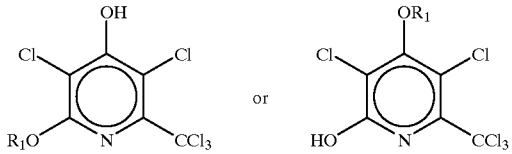

wherein $R_1$ is an alkyl group having at least two carbon atoms with an alkylating agent.

A still further aspect of the present invention is directed to producing a compound of formula II above wherein $R_2$ in position 4 is H and $R_2$ in position 6 is an alkyl which comprises reacting a compound represented by the formula I

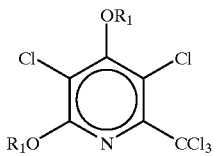

I wherein each $R_1$ is independently an alkyl group with $R_1$ in position 4 having at least two carbon atoms with a dealkylating agent to selectively dealkylate said compound in position 4.

Compounds of the present invention wherein the $R_1$ group located at position 4 is ethyl show anticancer activity. Accordingly, the present invention also relates to pharmaceutical compositions containing these compounds wherein the $R_1$ group located at position 4 is ethyl, and to methods of using such compounds in treating cancer in a mammal.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The present invention is concerned with pyridine compounds represented by the following formulae:

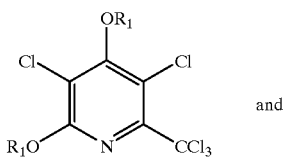

I and

II

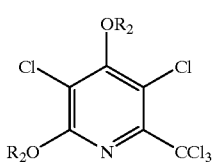

wherein
each $R_1$ is independently an alkyl group provided that at least one $R_1$ is an alkyl group containing at least two carbon atoms; and
each $R_2$ is independently H, acyl or an alkyl group having at least two carbon atoms or $R_2$ can be methyl in position 4 provided that $R_2$ is acyl in position 6.

The alkyl group typically contains 1 to 22 carbon atoms and preferably 2 to 22 carbon atoms.

The $R_2$ acyl groups can be straight or branched chained, can be unsubstituted or substituted such as with halogen such as Cl, Br and I, and/or include 5 and 6 membered rings. The ring moiety can be a carbocycle or a heterocycle including a hetero atom such as O, S or N. Typically, the acyl group contains 1–12 carbon atoms.

The present invention is also directed to compounds represented by the formula

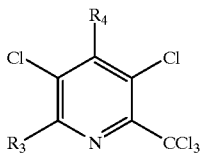

IV wherein one of $R_3$ or $R_4$ is Cl and the other of $R_3$ or $R_4$ is O-alkyl.

The alkyl group typically contains 1 to 22 carbon atoms. Preferably $R_3$ is O-alkyl and $R_4$ is Cl.

The compounds of formula IV can be produced by reacting 3,4,5,6-tetrachloro-2-(trichloromethyl)pyridine with an alcohol in the presence of a base and separating said compound from the reaction mixture. A typical base is NaOH. This process is preferably carried out under reflux with a typical alcohol being methanol.

Although many of the above precursor compounds do not exhibit any appreciable anti-cancer activity, it has been observed that at least a few of the precursor compounds show active anti-cancer activity. These compounds have the structure wherein at least the $R_1$ group located at position 4 is ethyl and include 3,5-dichloro-4,6-diethoxy-2-(trichloromethyl)pyridine and 3,5-dichloro-4-ethoxy-6-methoxy-2-(trichloromethyl)pyridine. Therefore, those compounds wherein at least the $R_1$ group at position 4 is ethyl or pharmaceutically acceptable salts thereof can be used in treating cancer in a mammal. However, these compounds are not as active as the acyl derivatives of 4-demethylpenclomedine according to copending U.S. patent application Ser. No. 60/116,675 filed Jan. 21, 1999 and entitled Acyl Derivatives of 4-Demethylpenclomedine, Use and Preparation Thereof, the entire disclosure of which is incorporated herein by reference, and also exhibit higher toxicity as compared to these acyl derivatives of DM-PEN.

These novel acyl derivatives of 4-demethylpenclomedine compounds are represented by the formula:

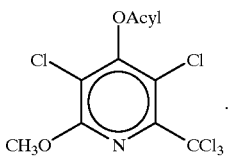

III and pharmaceutically acceptable salts thereof.

The acyl groups can be straight or branched chained, can be unsubstituted or substituted such as with halogen such as Cl, Br and I, and/or include 5 and 6 membered rings. The ring moiety can be a carbocycle or a heterocycle including a hetero atom such as O, S or N. Typically, the acyl group contains 1–12 carbon atoms.

Examples of such suitable acyl groups are the following, each of which has been evaluated for activity according to the present invention, and each has been characterized by mass spectroscopy:

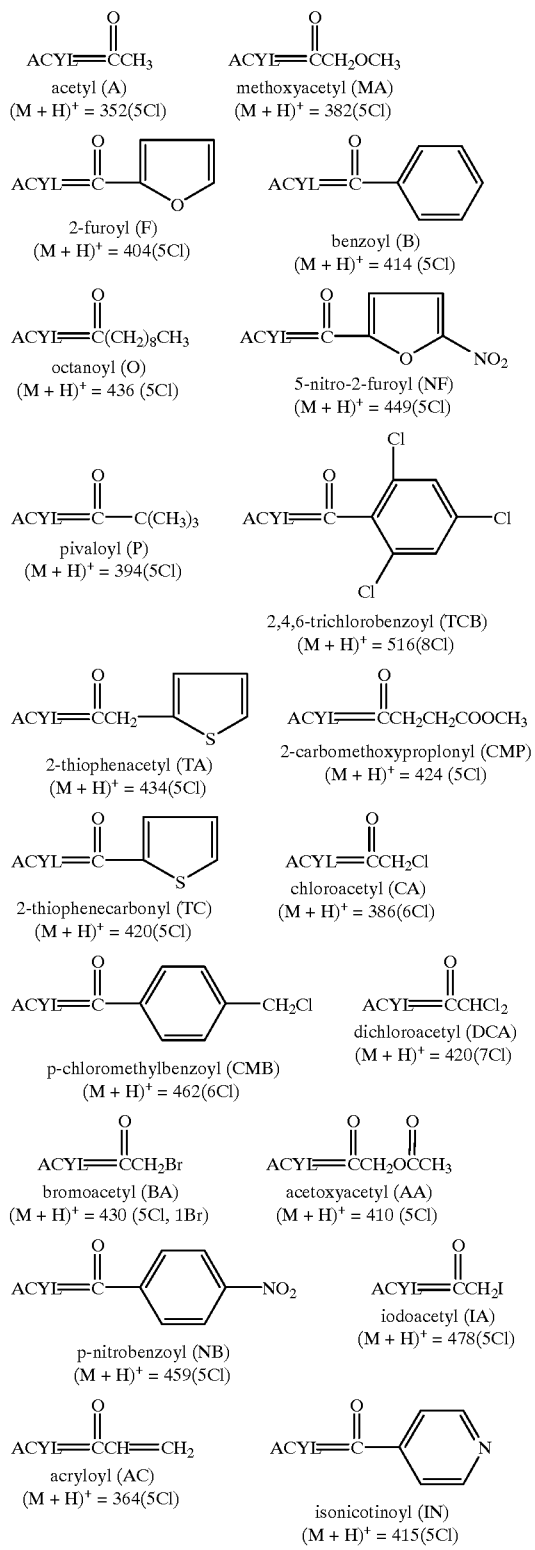

Examples of pharmaceutically acceptable acid addition salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulfonic, for example p-toluenesulfonic acid.

It has been found that the acyl compounds of formula III are surprisingly and advantageously useful in treating mammalian cancer, especially human cancer. These compounds have been shown to exhibit generally superior activity in comparison to 4-demethylpenclomedine and penclomedine. Moreover, these are believed to possess reduced toxicity in comparison to both demethylpenclomedine and penclomedine (PEN).

It is further noted, as will be discussed below, that the acyl compounds of formula III are not considered to be prodrug forms of DM-PEN. Both penclomedine (PEN) and DM-PEN are inactive as cytotoxic agents in vitro but must be metabolized to produce cytotoxicity, as demonstrated by their anticancer activity in vivo, which indicates that DM-PEN, as well as PEN, is a prodrug of the ultimate activated metabolite. The proposed mechanism by which PEN and DM-PEN exhibit cytotoxicity in vivo is shown in Scheme 1 and indicates that PEN and DM-PEN are on the same metabolic activation pathway, which includes a non-acylated, free radical activated for DNA crosslinking. In contrast, it is believed (Scheme 2) that the acyl derivatives (DM-ACYL-PEN) are converted via the liver to an acylated free radical (rather than a non-acylated free radical) and, as such, are not fully activated for DNA crosslinking but remain in a prodrug form as they exit the liver and enter the circulation. The partially activated acylated free radical is transported to cells via circulation and forms an adduct with nuclear DNA. Subsequently, the adduct is deacylated by general cellular esterases particularly in the tumor cell, which allows for in situ, full activation and possibly reduced generalized host toxicity in comparison to PEN and DM-PEN, both of which are fully activated in the liver for DNA adduction and crosslinking before being transported via circulation to tumor and non-tumor cells. Deacylation generates a 4-hydroxy moiety on the pyridine nucleus, which then tautomerizes via the enol-keto mechanism to produce an alpha-haloketo moiety at the 4,5-positions in which the 5-chloro function is activated for displacement by a nucleophilic moiety on the DNA for completion of a DNA crosslink, as shown in Scheme 2. This mechanism is further supported by the generally superior activity of the acyl derivatives in comparison to DM-PEN vs. both subcutaneously (s.c.)- and intracerebrally (i.c.)-implanted human MX-1 mammary tumor xenograft, s.c.-implanted human U251 CNS tumor xenograft, and both parent, and particularly, cyclophosphamide (CPA)-resistant lines of P388 leukemia, as shown in Tables 1–4 below.

Scheme 1
PROPOSED MECHANISM OF ACTION OF PEN AND 4-DEMETHYLPENCLOMEDINE (DM-PEN)

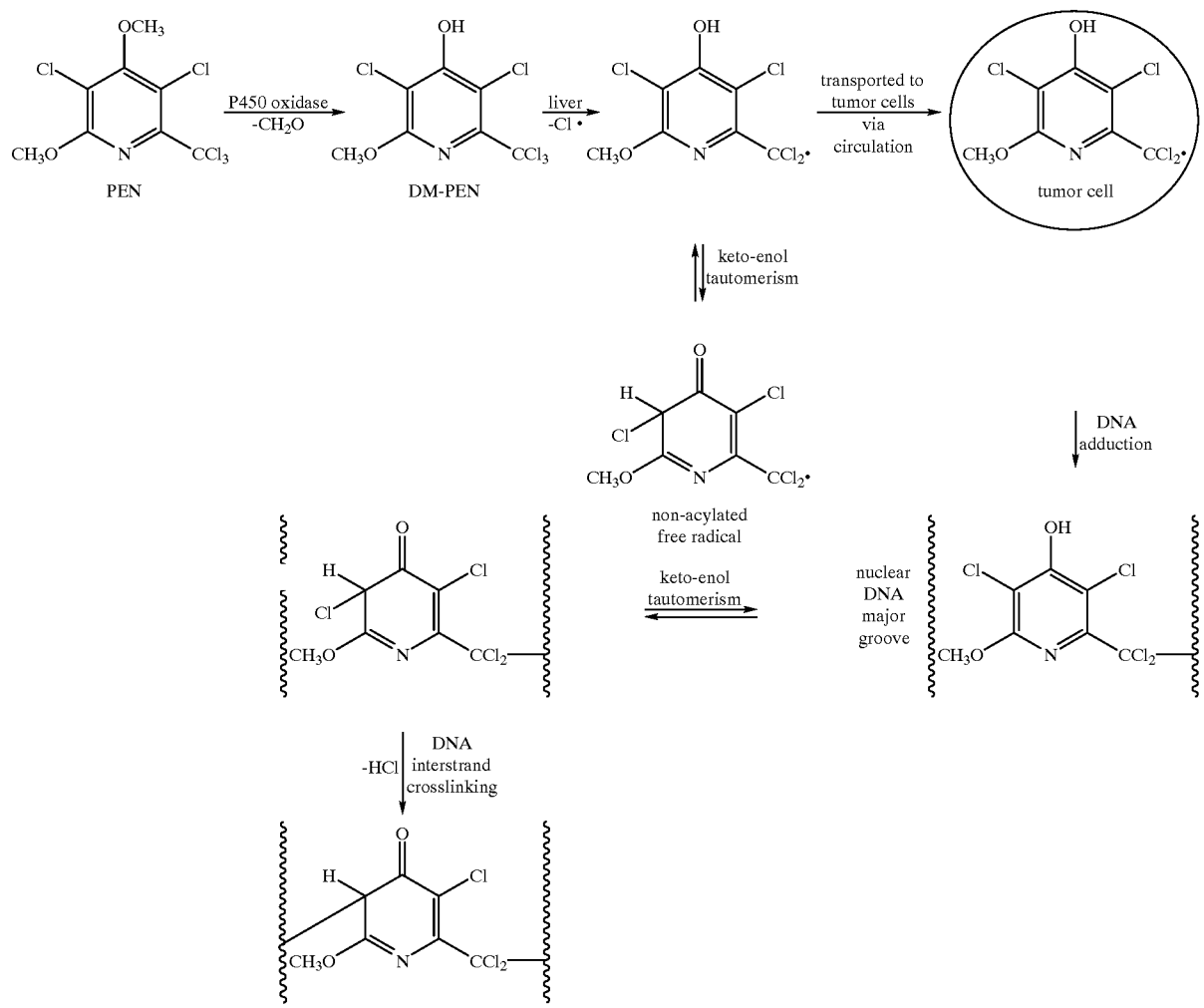

Scheme 2
PROPOSED MECHANISM OF ACTION OF 4-DEMETHYL-4-ACYL-PENCLOMEDINE (DM-ACYL-PEN)

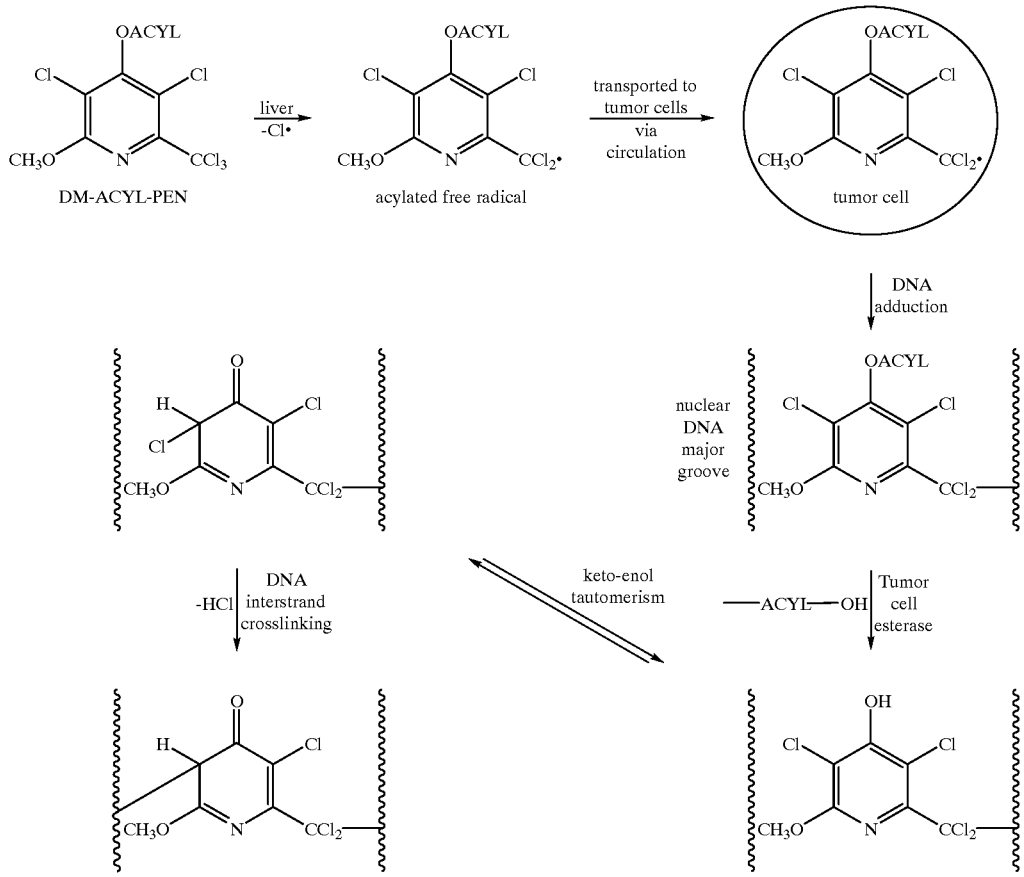

The acyl derivatives of DM-PEN can be synthesized by the following route that employs the pyridine compounds of the present invention.

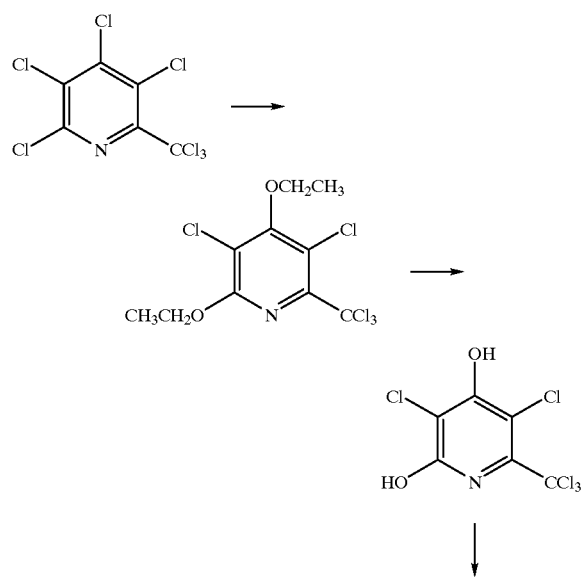

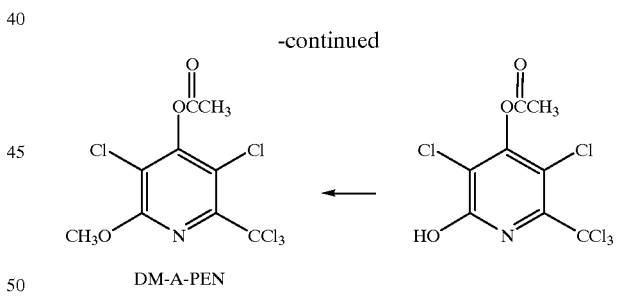

As illustrated above, the acyl derivatives of DM-PEN can be produced by reacting 3,4,5,6-tetrachloro-2-(trichloromethyl)pyridine with an alcohol in the presence of a base to produce the corresponding 3,5-dichloro-4,6-dialkoxy-2-(trichloromethyl)pyridine (i.e. compound of formula I), which in turn is reacted with a dealkylating agent such as anhydrous aluminum chloride to produce didemethylpenclomedine. (Compound of formula II wherein each $R_2$ is H.)

Of course, other dealkylating agents can be used if desired. The didemethylpenclomedine is then reacted with an acylating agent to form the corresponding acyl derivatives of demethylpenclomedine (i.e. compound of formula II wherein at least one $R_2$ is acyl), which is then reacted with an alkylating agent such as (trimethylsilyl)diazomethane to produce the acyl derivatives of DM-PEN.

It is understood that other acylating agents and alkylating agents can be used. Moreover, various reaction parameters such as temperature, relative amounts, and pressure can be selected by those skilled in the art once aware of the present disclosure.

In addition, compounds of formula I disclosed above can be produced by reacting a compound of the formula

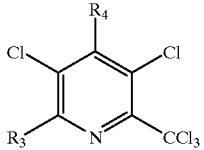

wherein one of $R_3$ and $R_4$ is Cl and the other of $R_3$ and $R_4$ is O-alkyl with an alcohol in the presence of a base.

A typical base is NaOH, and the reaction is typically carried out under reflux.

Moreover, compounds of formula I disclosed above can be produced by reacting a compound of the formula

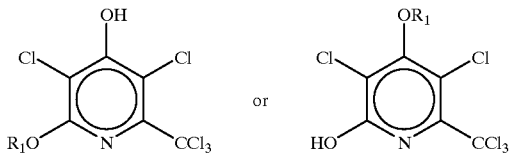

wherein $R_1$ is an alkyl group having at least two carbon atoms with an alkylating agent such as (trimethylsilyl)-diazomethane.

$R_1$ typically has 2–22 carbon atoms.

Compounds of formula II disclosed above wherein $R_2$ in position 4 is H and $R_2$ in position 6 is an alkyl can also be prepared by reacting a compound represented by the formula

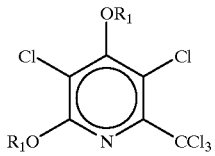

wherein each $R_1$ is independently an alkyl group with $R_1$ in position 4 having at least two carbon atoms with a dealkylating agent to selectively dealkylate said compound in position 4.

A typical dealkylating agent is dimethyl sulfoxide.

The reaction is typically carried out under elevated temperatures such as about 140 to about 160° C., an example of which is about 150° C.

The alkyl group in the 4 position typically contains 2–22 carbon atoms, and preferably 2–6 carbon atoms, examples of which are ethyl and n-butyl. The alkyl group is preferably straight chained. For instance under the conditions employed in Example 3 below, using isopropyl did not achieve the desired result.

The above process is suitable for producing 4-demethylpenclomedine which in turn can be used to produce the above disclosed acyl derivatives of 4-demethylpenclomedine.

Novel precursors for producing the acyl derivatives of the present invention are represented by the following formulae:

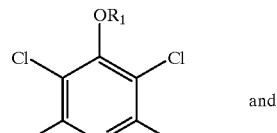

and

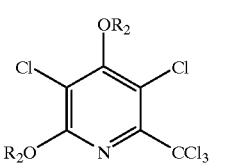

wherein each $R_1$ is independently an alkyl group provided that at least one $R_1$ is an alkyl group containing at least two carbon atoms; and each $R_2$ is independently H, acyl or alkyl having at least two carbon atoms or $R_2$ can be methyl in position 4 provided that $R_2$ is acyl in position 6.

The alkyl group typically contains 1 to 22 carbon atoms and preferably 2 to 22 carbon atoms.

The $R_2$ acyl groups can be straight or branched chained, can be unsubstituted or substituted such as with halogen such as Cl, Br and I, and/or include 5 and 6 membered rings. The ring moiety can be a carbocycle or a heterocycle including a hetero atom such as O, S or N. Typically, the acyl group contains 1–12 carbon atoms.

Although many of the above precursor compounds do not exhibit any appreciable anti-cancer activity, it has been observed that at least a few of the precursor compounds show active anti-cancer activity. These compounds have the structure wherein at least the $R_1$ group located at position 4 is ethyl and include 3,5-dichloro-4,6-diethoxy-2-(trichloromethyl)pyridine and 3,5-dichloro-4-ethoxy-6-methoxy-2-(trichloromethyl)pyridine. Therefore, those compounds wherein at least the $R_1$ group at position 4 is ethyl or pharmaceutically acceptable salts thereof can be used in treating cancer in a mammal. However, these precursor compounds are not as active as the acyl compounds of the present invention and also exhibit higher toxicity as compared to acyl compounds of the present invention.

The following non-limiting examples are presented to further illustrate the present invention.

EXAMPLE 1

The procedure is as follows: 3,4,5,6-tetrachloro-2-(trichloromethyl)pyridine (4.00 g; 11.96 mm), sodium hydroxide (1.92 g; 48 mm) and anhydrous ethanol (60 ml) are refluxed for 1-½ hr. The reaction mixture is concentrated to dryness, and the residue is extracted twice with methylene chloride (2×60 ml). The extract is washed with water and the organic layer, after drying over $MgSO_4$, is filtered and concentrated to dryness. The resulting crude product is purified by column chromatography on silica gel (230–400 mesh) and eluted with hexanes. Fractions are collected and analyzed by TLC, and those containing the product are combined and evaporated. The residue is dried over $P_2O_5$, in vacuo: yield: 3.18 g (75%); white solid; m.p. 27–28° C., 3,5-dichloro-4,6-diethoxy-2-(trichloromethyl)pyridine. This product (1 g) is dissolved in 20 ml of anhydrous methylene chloride. To this solution anhydrous aluminum chloride (1.0 g) is added, and the reaction mixture is stirred for 1 hr at room temperature. The reaction mixture is evaporated to dryness in vacuo, and the crude product is purified by column chromatography on silica gel (230–400 mesh) with elution with 5:1 chloroform:methanol. Fractions are collected and analyzed by TLC, and those containing the product are combined and evaporated. The residue is dried in vacuo over $P_2O_5$: yield: 818 mg (97%), didemethylpenclomedine. This product (100 mg) is dissolved in 2 ml anhydrous pyridine. To this solution acetic anhydride (0.03 ml) is added dropwise. The reaction mixture is stirred for 6 hrs at room temperature and concentrated to dryness in vacuo. The crude product is purified by column chromatography on silica gel (230–400 mesh) by elution with 95:5 chloroform-methanol. The desired fractions are combined based on thin layer chromatographic analysis, concentrated to dryness and dried in vacuo over $P_2O_5$. Yield: 8 mg (7%); FABMS analysis, m/z 338 (5 Cl), 4-demethyl-4-acetyl-6-demethylpenclomedine. This product (8 mg) is dissolved in 1 ml methanol and treated with excess diazomethane or (trimethylsilyl)diazomethane. After 30 min at room temperature, the solution was analyzed by TLC, which indicated quantitative conversion to DM-A-PEN, and evaporated to dryness in vacuo, yielding the target structure.

EXAMPLE 2

As shown in the reaction scheme below, the ethyl analog of DM-PEN, DM-E-PEN, is prepared from 3,5-dichloro-4,6-diethoxy-2-(trichloromethyl)pyridine by a procedure identical to that used for DM-PEN, and its structure is confirmed by mass spectral analysis and its purity by TLC analysis. DM-E-PEN in acetone is treated with excess (trimethylsilyl)diazomethane and stirred 45 min at room temperature. Evaporation gives a residue that is purified by silica gel column chromatography, giving 6-demethyl-6-ethyl-PEN (6-DM-6-E-PEN) whose structure is confirmed by FABMS.

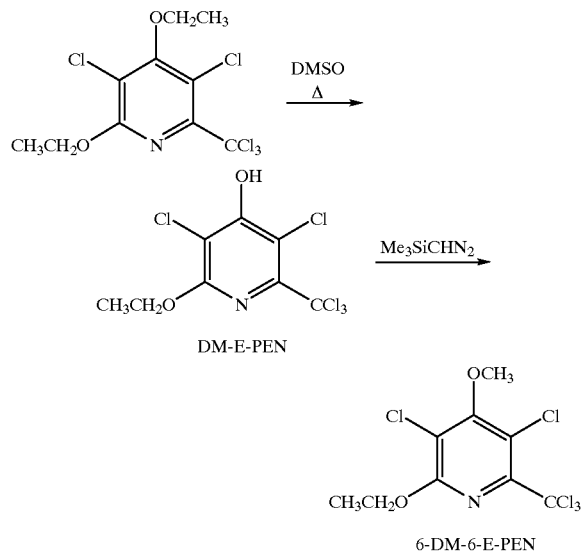

The following structures are prepared from 3,4,5,6-tetrachloro-2-(trichloromethyl)pyridine by reaction with sodium hydroxide in refluxing methanol. Evaporation, extraction of the residue with dichloromethane, washing the extract with water, drying over magnesium sulfate and evaporation give a residue that is separated by silica gel column chromatography in hexane. TLC analysis of column fractions, combining of appropriate fractions, and evaporation give two products, 6-demethoxy-6-chloro-PEN (6-DMO-6-C-PEN) and 4-demethoxy-4-chloro-PEN (4-DMO-4-C-PEN) in a ratio of 9:1. Structures are confirmed by $^1$H-NMR and FABMS analysis and are shown here:

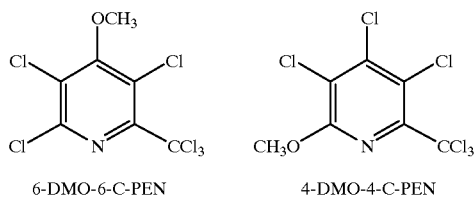

4-DMO-4-C-PEN is converted to 4-DM-4-E-PEN by refluxing in a solution of sodium hydroxide in ethanol, with purification being accomplished by silica gel column chromatography in hexane and subsequent characterization by $^1$H-NMR and FABMS analysis:

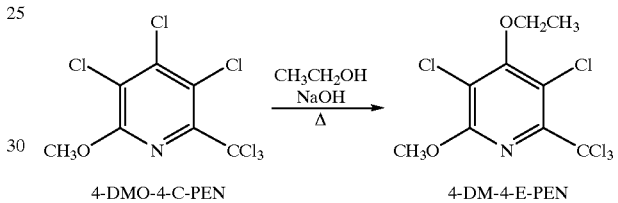

EXAMPLE 3

Preparation of 4-Demethylpenclomedine

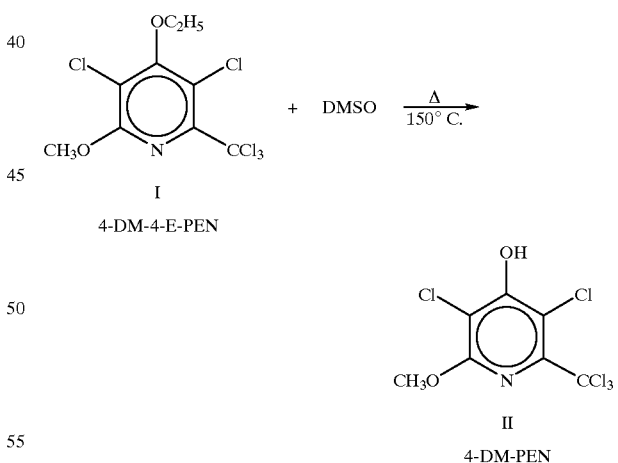

Compound I (4-DM-4-E-PEN 510 mg, 1.5 mmoles) is dissolved in anhydrous DMSO (3 ml) and heated at about 150° C. for about 1 hr. The solution is lyophilized, and the crude product is purified by column chromatography. The column is packed with silica gel (230–400 mesh) and eluted with 9:1 chloroform-methanol. The desired portions are collected, concentrated and dried in vacuo over $P_2O_5$.

Yield: $F_1$ 252 mg (starting material) $F_2$ 166 mg (desired product) (35.5%)

EXAMPLE 4

Procedure for Preparation of Didemethyl-diacetyl-PEN (DDM-DA-PEN) from Didemethyl-PEN (DDM-PEN)

About 950 mg of didemethylpenclomedine (DDM-PEN) prepared from didemethyl-diethyl-PEN in the manner described above in Example 1 are dissolved in 2 ml of acetic anhydride and 2 drops of pyridine and heated for about 10 min. at a low setting on a hot plate and allowed to stand for about 30 min. at room temperature. Excess acetic anhydride is removed by evaporation in vacuo, and the residue is crystallized from hexane, yielding about 600 mg of DDM-DA-PEN as white crystals.

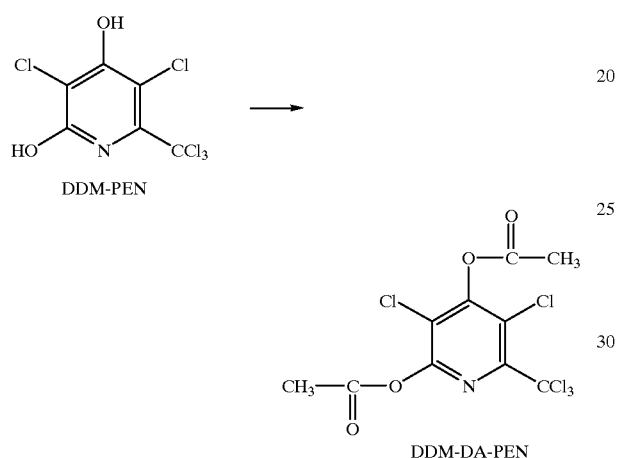

EXAMPLE 5

Procedure for Preparation of DM-A-PEN from Didemethyl-diacetyl-PEN (DDM-DA-PEN)

DDM-DA-PEN prepared according to the procedure of Example 4 (20 mg) in 2 ml of a solution of 0.1 ml concentrated hydrochloric acid in 10 ml methanol is stirred for about 2 hours at room temperature and evaporated to dryness in vacuo. The residue is treated with excess (trimethylsilyl)diazomethane, and the solution is allowed to stand at room temperature for 2 hours and evaporated in vacuo. The residue is separated by preparative thin-layer chromotography (TLC) on a 4" analytical silica gel plate in hexane:dichloromethane (1:1). The major UV-visible band ($R_f$ 0.9) is eluted with acetone, and evaporation gives 9 mg of a product that is identical to authentic DM-A-PEN upon co-TLC in hexane-dichloromethane (1:1). The yield is 49%.

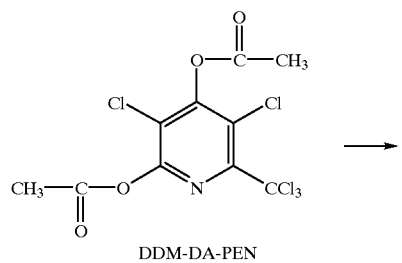

DDM-DA-PEN

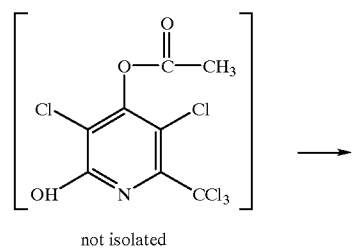

not isolated

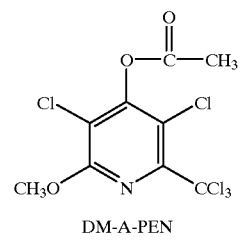

DM-A-PEN

Antitumor Activity

The antitumor activity data of the acyl derivatives of DM-PEN vs MX-1 human mammary tumor xenograft implanted s.c. or i.c. with intraperitoneal (i.p.) or oral drug treatment are shown in Table 1 below. For certain lipophilic derivatives, such as DM-B-PEN, the benzoyl derivative, it is apparent from the results that oral absorption was poor, yielding low antitumor activity, whereas high activity was observed following i.p. administration.

Other derivatives, such as DM-MA-PEN (methoxyacetyl), DM-O-PEN (octanoyl), DM-F-PEN (2-furoyl) and DM-TC-PEN (2-thiophenecarbonyl) demonstrated significant activity against i.c.-implanted tumor in comparison to PEN and DM-PEN, as shown in Table 2, with cures being observed for two of the acylated derivatives but not for PEN or DM-PEN.

One derivative, DM-A-PEN (acetyl), was evaluated against other s.c.-implanted human tumor xenografts, as shown in Table 3, with moderate to modest activity being observed against U251 human CNS tumor, ZR-75–1 and MCF7 human mammary tumors, CAKI-1 human renal tumor, NCI-H82 small cell lung tumor and HT29 human colon tumor. The activity of DM-A-PEN was compared with the activity of PEN and DM-PEN against P388 murine leukemia (P388/0) and three resistant lines (P388/L-PAM, P388/CPA and P388/BCNU; melphalan, cyclophosphamide and carmustine, resp.), as shown in Table 4.

TABLE 1

Summary of the In Vivo Antitumor Activity of
DM-ACYL-PEN Against Human MX-1 Mammary Tumor

| DM-ACYL-PEN | Tumor Site[a] | Optimal IP Dosage (<$LD_{10}$) (mg/kg/dose) | Schedule | Median % ILS (dying mice only) | T–C[b] (days) | Tumor-Free-Surv/Total |
|---|---|---|---|---|---|---|
| DM-A-PEN | sc MX-1 | 90 | Days 12–16 | —[c] | >41.0 | 5/5 |
| " | sc MX-1 | 60 | Days 14–18 | — | >38.3 | 4/5 |
| " | sc MX-1 | 135[d,e] | Days 13–17 | — | >38.5 | 5/5 |
| " |  | 60 ($LD_{20}$) | Days 15–19 | — | >37.2 | 3/5 |
| " | ic MX-1 | 60 | Days 1–5 | +60 |  |  |
| " |  | 135[d,e] | Days 1–5 | +88 | — |  |
| DM-B-PEN | sc | 135 | Days 13–17 | — | -1.4 | 0/5 |
| " | sc | 135 | Days 11–15 | — | >42.7 | 5/5 |
| " | ic | 135 | Days 1–5 | 84 | — | 0/5 |
| " | ic | 135[d] | Days 1–5 | +12 | — | 0/5 |
| DM-P-PEN | sc | 135[d,e] | Days 13–17 | — | 0.9 | 0/5 |
| " | sc | 135[e] | Days 11–15 | — | >42.7 | 5/5 |
| " | ic | 135 | Days 1–5 | +64 | — | 0/5 |
| " | ic | 135[d] | Days 1–5 | +20 | — | 0/5 |
| DM-CMP-PEN | sc | 135[d,e] | Days 13–17 | — | >38.5 | 2/5 |
| " | sc | 135 | Days 11–15 | — | >42.7 | 3/5 |
| " | ic | 90[d] | Days 1–5 | +76 | — | 1/5 |
| " | ic | 90 | Days 1–5 | +87 | — | 1/5 |
| DM-CA-PEN | sc | 60 | Days 12–16 | — | >41.0 | 3/5 |
| " |  | 135[d,e] | Days 12–16 | — | >41.0 | 5/5 |
| " | ic | 135 | Days 1–5 | +84 | — | 2/5 |
| DM-BA-PEN | sc | 135 | Days 12–16 | — | >41.0 | 2/5 |
| DM-IA-PEN | sc | 60 ($LD_{20}$) | Days 12–16 | — | 20.3 | 1/5 |
| DM-MA-PEN | sc | 135[d,e] | Days 12–16 | — | >41.0 | 5/5 |
| " | ic | 90[d] | Days 1–5 | +110 | — | 1/5 |
| " | ic | 90 | Days 1–5 | +126 | — | 1/5 |
| DM-O-PEN | ic | 90 | Days 1–5 | +121 |  | 0/5 |
| DM-TCB-PEN | ic | 135 | Days 1–5 | +92 |  | 1/5 |
| DM-CMB-PEN | ic | 90 | Days 1–5 | +73 | — | 0/5 |
| DM-AA-PEN | ic | 135[d,e] | Days 1–5 | +115 | — | 2/5 |
| " | ic | 135[e] | Days 1–5 | +67 | — | 0/5 |
| DM-F-PEN | sc | 90 | Days 12–16 | — | >41.2 | 5/5 |
| " | ic | 135 | Days 1–5 | +108 | — | 2/5 |
| DM-NF-PEN | sc | 90 | Days 12–16 | — | >41.2 | 4/5 |
| " | ic | 135 | Days 1–5 | +59 | — | 0/5 |
| DM-AC-PEN | sc | 60 | Days 12–16 | — | 30.0 | 1/5 |
| " | ic | 60 | Days 1–5 | 55 | — | 0/5 |
| DM-TA-PEN | sc | 90 | Days 12–16 | — | >41.2 | 3/5 |
| " | ic | 90 | Days 1–5 | +75 | — | 0/5 |
| DM-TC-PEN | sc | 90 | Days 12–16 | — | >41.2 | 4/5 |
| " | ic | 135 | Days 1–5 | +100 | — | 0/5 |
| DM-DCA-PEN | sc | 135[e] | Days 12–16 | — | >38.6 | 2/5 |
| DM-IN-PEN | sc | 90 ($LD_{20}$) | Days 12–16 | — | >38.6 | 3/5 |
| DM-NB-PEN | sc | 135[e] | Days 12–16 | — | >38.6 | 5/5 |

[a]Athymic mice (Ncr-nu) were implanted with human MX-1 mammary tumor (either ic with $10^6$ cells of sc with 30–40 mg fragments).
[b]The difference in the median of times poststaging for tumors of the treated (T) groups to double twice in mass compared to the median of the control (C) group.
[c]% ILS values are meaningless, since mice were sacrificed when their tumors reached 4 g.
[d]Oral treatment (by gavage).
[e]Highest dosage tested.

A=acetyl
B=benzoyl
P=pivaloyl
CMP=2-carbomethoxypropionyl
CA=chloroacetyl
BA=bromoacetyl
LA=iodoacetyl
MA=methoxyacetyl
O=octanoyl
TCB=2,4,6-trichlorobenzoyl CMB=p-chloromethylbenzoyl
AA=acetoxyacetyl
F=2-furoyl
NF=5-nitro-2-furoyl
AC=cryloyl
TA=thiophenacetyl
TC=thiophenecarbonyl
DCA=dichoroacetyl
IN=isonicotinoyl
NB=p-nitrobenzoyl

TABLE 2

Comparative Activity of PEN, DM-PEN and DM-ACYL-PEN Against I.C.-Implanted Human MX-1 Mammary Tumor at Optimal Doses (LD10 or Less) and Schedule (QD1-5) Administered I.P.

| PEN | | DM-PEN | | DM-ACYL-PEN | |
|---|---|---|---|---|---|
| Median % ILS[e] | Survivors | Median % ILS[e] | Survivors | Median % IL5[e] | Survivors |
| 88 | 0/5 | 60 | 0/5 | 126[a] | 1/5 |
| | | | | 121[b] | 0/5 |
| | | | | 108[c] | 2/5 |
| | | | | 100[d] | 0/5 |

[a]DM-MA-PEN
[b]DM-O-PEN
[c]DM-F-PEN
[d]DM-TC-PEN
[e]based on dying mice only

TABLE 3

Summary of the In Vivo Antitumor Activity of DM-Acetyl-PEN

| Tumor[a] | Optimal IP Dosage (<$LD_{10}$) (mg/kg/dose) | Schedule | T–C[b] (days) | Tumor-Free-Surv/Total |
|---|---|---|---|---|
| sc ZR-75-1 | 90 | Days 8–12 | 14.1 | 0/5 |
| " | 60 | Days 10–14 | 10.6 | 0/5 |
| sc MCF7 | 60 | Days 14–18 | 7.1 | 0/5 |
| sc UISO-BCA-1 | 90 | Days 16–20 | -2.4 | 0/5 |
| sc HT29 | 90 | Days 14–18 | 5.8 | 0/5 |
| sc NCI-H82 | 60 | Days 13–17 | 7.2 | 0/5 |
| sc NCI-H460 | 90 | Days 6–10 | -0.6 | 0/5 |
| sc U251 | 90 | Days 19–23 | 15.7 | 0/5 |
| sc SF-295 | 90 | Days 9–13 | 0.7 | 0/5 |
| sc CAKI-1 | 90 | Days 19–23 | 8.4 | 0/5 |
| sc OVCAR-5 | 90 | Days 12–16 | 4.0 | 0/5 |
| sc SK-MEL-28 | 90 | Days 8–12 | 0.7 | 0/5 |

[a]Athymic mice (Ncr-nu) were implanted either ic with $10^6$ human MX-1 mammary tumor cells or sc with fragments of human tumors (MX-1, UISO-BCA-1, MCF7, and ZR-75-1 mammary; HT29 colon, NCI-H460 nonsmall cell lung; OVCAR-5 ovarian; CAKI-1 renal; SK-MEL-28 melanoma; NCI-H82 small cell lung; U251 and SF-295 CNS).
[b]The difference in the median of times poststaging for tumors of the treated (T) groups to double twice in mass compared to the median of the control (C) group.

TABLE 4

EVALUATION OF THE ANTITUMOR ACTIVITY OF PENCLOMEDINE, DM-PEN, AND DM-A-PEN AGAINST P388/0, P3888/L-PAM, P388/CPA, AND P388/BCNU LEUKEMIAS IN CDEF1 FEMALE MICE

IMPLANT: IP, 1.0E+06 CELLS

| | | | p388/0 (TUMOR BURDEN AT START OF Rx = ca 6.0E+00 CELLS) THERAPEUTIC RESPONSE* | | | | P388/L-PAM (TUMOR BURDEN AT START OF Rx = ca 6.3E+06 CELLS) THERAPEUTIC RESPONSE* | | | |
|---|---|---|---|---|---|---|---|---|---|---|
| TREATMENT: IP | | | | | | APPROX. NET | | | | APPROX. NET |
| AGENT | DOSAGE (MG/KG/DOSE) | SCHEDULE | 50-DAY SURV./TOTAL | MEDIAN DAY OF DEATH | % ILS | LOG10 CHANGE IN TUMOR BURDEN AT END OF Rx** | 50-DAY SURV./TOTAL | MEDIAN DAY OF DEATH | % ILS | LOG10 CHANGE IN TUMOR BURDEN AT END OF Rx** |
| L-PAM (melphalan) (NSC 8806) | 20.0 | Q1D × 1 (1) | 6/6 | 34.0 | +200 | ca −6.6 | 0/6 | 16.0 | +14 | −1.6 |
| | 15.0 | | 6/6 | — | — | — | 0/6 | 16.0 | +14 | −1.6 |
| CPA (cyclophosphamide) (NSC 26271) | 265.0 | Q1D × 1 (1) | 6/6 | — | — | — | | | | |
| | 175.0 | | 1/6 | 30.0 | +172 | ca −6.6 | | | | |
| BCNU (carmustine) (NSC 409962) | 30.0 | Q1D × 1 (1) | 6/6 | — | — | — | | | | |
| | 20.0 | | 3/6 | 27.0 | +145 | ca −6.6 | | | | |
| PEN | 135.0 | Q1D × 5 (1) | 0/6 | 21.0 | +0 | −4.6 | 0/6 | 13.0 | −8 | +1.5 |
| | 90.0 | | 0/6 | 16.0 | +45 | −0.6 | 0/6 | 13.0 | −8 | +1.6 |
| | 60.0 | | 0/6 | 14.6 | +31 | +0.4 | 0/8 | 14.0 | 0 | +1.4 |
| DM-PEN | 135.0 | Q1D × 5 (1) | 0/6 | 8.5 | −23 | TOXIC | 0/6 | 13.5 | −4 | (LD33) +1.5 |
| | 90.0 | | 0/6 | 19.0 | +72 | −3.1 | 0/6 | 13.0 | −8 | +1.5 |
| | 60.0 | | 0/6 | 16.0 | +45 | −0.8 | 0/6 | 13.5 | −4 | +1.5 |
| DM-A-PEN | 135.0 | Q1D × 5 (1) | 0/6 | 28.5 | +150 | (LD33) ca −6.6 | 0/6 | 10.0 | +35 | (LD17) −0.8 |
| | 90.0 | | 0/6 | 21.5 | +95 | −5.0 | 0/6 | 16.0 | +14 | +1.2 |
| | 60.0 | | 0/6 | 19.0 | +72 | −3.1 | 0/6 | 16.0 | +14 | +1.2 |

TABLE 4-continued

EVALUATION OF THE ANTITUMOR ACTIVITY OF PENCLOMEDINE, DM-PEN, AND DM-A-PEN AGAINST P388/0, P3888/L-PAM, P388/CPA, AND P388/BCNU LEUKEMIAS IN CDEF1 FEMALE MICE

IMPLANT: IP, 1.0E+06 CELLS

| TREATMENT: IP | | | p388/CPA (TUMOR BURDEN AT START OF Rx = ca 3.7E+06 CELLS) THERAPEUTIC RESPONSE* | | | | P388/BCNU (TUMOR BURDEN AT START OF Rx = ca 6.3E+06 CELLS) THERAPEUTIC RESPONSE* | | | |
|---|---|---|---|---|---|---|---|---|---|---|
| AGENT | DOSAGE (MG/KG/ DOSE) | SCHEDULE | 50-DAY SURV./ TOTAL | MEDIAN DAY OF DEATH | % ILS | APPROX. NET LOG10 CHANGE IN TUMOR BURDEN AT END OF Rx** | 50-DAY SURV./ TOTAL | MEDIAN DAY OF DEATH | % ILS | APPROX. NET LOG10 CHANGE IN TUMOR BURDEN AT END OF Rx** |
| L-PAM (melphalan) (NSC 8806) | 20.0 15.0 | Q1D × 1 (1) | | | | | | | | |
| CPA (cyclophos- phamide) (NSC 26271) | 265.0 175.0 | Q1D × 1 (1) | 0/6 0/6 | 14.0 12.0 | +27 +9 | −1.7 −0.6 | | | | |
| BCNU (carmustine) (NSC 400962) | 30.0 20.0 | Q1D × 1 (1) | | | | | 0/6 0/6 | 8.5 9.0 | −6 0 | +0.4 0 |
| PEN | 135.0 90.0 60.0 | Q1D × 5 (1) | 0/6 0/6 0/6 | 10.5 10.5 10.5 | −5 −5 −5 | +1.7 +1.7 +1.7 | 0/6 0/6 0/6 | 11.5 9.0 8.6 | +27 0 −6 | +1.2 +1.7 +1.8 |
| DM-PEN | 135.0 90.0 60.0 | Q1D × 5 (1) | 0/6 0/6 0/6 | 14.5 17.0 13.5 | +31 +54 +22 | +0.3 −1.1 +0.9 | 0/6 0/6 0/6 | 17.0 140 12.0 | +68 (LD17) +55 +33 | −3.1 −0.8 +0.8 |
| DM-A-PEN | 135.0 90.0 60.0 | Q1D × 5 (1) | 0/6 0/6 0/6 | 25.0 20.5 17.0 | +127 +85 +54 | −5.7 −3.1 −1.1 | 0/6 0/6 1/6 | 21.0 16.0 13.0 | +133 (LD17) +77 +44 | −4.1 −2.3 0 |

P388/0, P388/L-PAM, P388/CPA, AND P388/BCNU ASCITES: TUMOR SOURCES: PS 10/A/04F311, P388/L-PAM 02/1/04F 1513, P388/CPA 05/1/ 04F612, AND P388/BCNU 03/A/0-4F18T1; IMPLANTED: 10/30/96; CD2F1 - FEMALE - CHARLES RIVER, PORTAGE
*BASED ON MEDIAN DAY OF DEATH (DYING MICE ONLY).
**LOG10 CHANGE = NET LOG CHANGE IN VIABLE TUMOR CELL PORPULATION AT THE END OF Rx AS COMPARED TO THE START OF rx: e.g., A −6 LOG CHANGE MEANS THAT THERE WAS A 99.9999% RDUCTION AND A +3 LOG CHANGE MEANS THERE WAS A 1,000- FOLD INCREASE IN TUMOR BURDEN AT END OF Rx.

At the highest nontoxic doses evaluated, DM-A-PEN was observed to be more active than DM-PEN against P388/0 (by a 1.9 log cell kill), P388/CPA (by an impressive 4.6 log cell kill) and P388/BCNU (by a 1.5 log cell kill). Although DM-A-PEN was only slightly more active than PEN against P388/0 (by a 0.4 log cell kill), it was much more active than PEN against P388/CPA (by a 7.4 log cell kill) and more active against P388/BCNU (by a 3.5 log cell kill). The much higher activity of DM-A-PEN against P388/CPA suggests that this agent may be active against other CPA-resistant tumors, and the consistently higher activity of DM-A-PEN against P388/0, P388/CPA and P388/BCNU also suggests that it is not a prodrug of DM-PEN. Although DM-A-PEN was slightly more active than PEN or DM-PEN against P388/L-PAM (by a 0.2–0.3 log cell kill), none of the three showed significant activity in this tumor model.

Compounds of formula I wherein the $R_1$ at position 4 is ethyl (referred to as 4-ethyl pyridines) or the acyl derivatives of 4-demethylpenclomedine can be used alone or in appropriate association, and also may be used in combination with pharmaceutically acceptable carriers and other pharmaceutically active compounds such as other cancer treatment drugs. The 4-ethyl pyridines and acyl derivatives of 4-demethylpenclomedine also may be used as their acid addition salts. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The 4-ethyl pyridines and/or acyl derivatives of 4-demethylpenclomedine alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient,.and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238–250 (1982) and *ASHP Handbook on Injectable Drugs*, Toissel, 4th ed., 622–630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an animal are available, and, although more than one route can be used to administer a particular compound, a particular route can provide a more immediate and more effective reaction than another route.

The present invention further provides a method of treating cancer in a mammal, especially humans. The method comprises administering an effective treatment amount of 4-ethylpyridines to the mammal.

As regards these applications, the present inventive method includes the administration to an animal, particularly a mammal, and more particularly a human, of a therapeutically effective amount of the compound effective in the inhibition of neoplasia and tumor growth.

The compound and compositions of the present invention can be administered to treat a number of cancers, including leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The method of the present invention is particularly applicable in the treatment of brain, colon, renal and mammary tumors, and preferably colon, brain and mammary tumors. The method of the present invention can be practiced on mammals, particularly humans.

The dose administered to an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to effect the desired response. The preferred dosage is the amount which results in maximum inhibition of cancer, without unmanageable side effects.

The total amount of the compound of the present invention administered in a typical treatment is preferably between about 60 mg/kg and about 2000 mg/kg of body weight for mice, and between about 5 mg/kg and about 100 mg/kg of body weight, and more preferably between 5 mg/kg and about 20 mg/kg of body weight for humans. This total amount is typically, but not necessarily, administered as a series of smaller doses over a period of from about one day to about 24 months, and preferably over a period of 28 days to about 12 months.

The size of the dose also will be determined by the route, timing and frequency of administration as well as the existence, nature, and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

The method of the present invention comprises further administering of a chemotherapeutic agent other than the 4-ethyl pyridines and/or acyl derivatives of the present invention. Any suitable chemotherapeutic agent can be employed for this purpose. The chemotherapeutic agent is typically selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, thioguanine, floxuridine, fludarabine, cladribine and L-asparaginase.

Examples of chemotherapeutic agents that are natural products include actinomycin D, bleomycin, camptothecins, daunomycin, doxorubicin, etoposide, mitomycin C, TAXOL (paclitaxel), taxotere, teniposide, vincristine, vinorelbine, mithramycin, idarubicin, MITHRACIN™ (plicamycin), and deoxycoformycin.

An example of a hormonal chemotherapeutic agent includes tamoxifen. Examples of the aforesaid miscellaneous chemotherapeutic agents include mitotane, mitoxantrone, vinblastine, and levamisole.

The foregoing description of the invention illustrates and describes the present invention Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A compound represented by the formulae

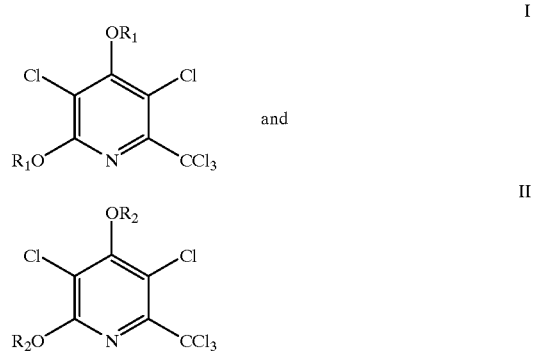

wherein
  each $R_1$ is independently an alkyl group provided that at least one $R_1$ is an alkyl group containing at least two carbon atoms; and
  each $R_2$ is independently selected from the group consisting of H, acyl and alkyl having at least two carbon atoms or $R_2$ can be methyl in position 4 when $R_2$ is acyl in position 6.

2. The compound of claim 1 wherein the alkyl group has 1 to 22 carbon atoms.

3. The compound of claim 1 wherein the alkyl group has 2–22 carbon atoms.

4. The compound of claim 1 wherein the acyl group is selected from the group consisting of optionally substituted straight chained acyl groups, optionally substituted branched chained acyl groups, 5 membered ring compounds and 6 membered ring compounds.

5. The compound of claim 2 wherein the ring compounds are carbocycle or heterocycle comprising at least one hetero atom selected from the group consisting of O, S and N.

6. The compound of claim 1 wherein the acyl group contains 1 to 12 carbon atoms.

7. The compound of claim 1 wherein the acyl group is selected from the group consisting of formyl, acetyl, methoxyacetyl, furoyl, benzoyl, octanoyl, nitro-furoyl, pivaloyl, trichlorobenzoyl, thiophenacetyl, carbomethoxypropionyl, thiophenecarbonyl, chloracetyl, chloromethylbenzoyl, dichloroacetyl, bromoacetyl, acetoxyacetyl, nitrobenzoyl, iodoacetyl, acryloyl, and isonicotinoyl.

8. The compound of claim 1 wherein the acyl group is acetyl.

9. The compound of claim 1 being 3,5-dichloro-4,6-diethoxy-2-(trichloromethyl)pyridine.

10. The compound of claim 1 being 3,5-dichloro-4-ethoxy-6-methoxy-2-(trichloromethyl)pyridine.

11. A pharmaceutical composition comprising the compound of claim 9 or an addition salt thereof and a pharmaceutically acceptable carrier.

12. A pharmaceutical composition comprising the compound of claim 10 or an addition salt thereof and a pharmaceutically acceptable carrier.

13. A method for producing an acyl derivative of 4-demethylpenclomedine represented by the formula

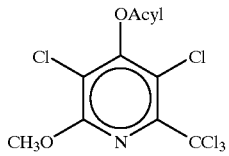

III which comprises:
a) reacting 3,4,5,6-tetrachloro-2-(trichloromethyl)pyridine with an alcohol in the presence of a base to produce the corresponding 3,5-dichloro-4,6-dialkoxy-2-(trichloromethyl)pyridine,
b) reacting the product obtained from a) with a dealkylating agent to produce didemethylpenclomedine;
c) reacting the product obtained from b) with an acylating agent to form the corresponding 4-acyl-6-demethylpenclomedine;
d) reacting the product from c) with an alkylating agent to produce its desired acyl derivative.

14. The method of claim 13 wherein the dealkylating agent is anhydrous aluminum chloride.

15. The method of claim 13 wherein the acylating agent is a carboxylic acid anhydride or carboxylic acid halide.

16. The method of claim 13 wherein the alkylating agent is (trimethylsilyl)diazomethane or diazomethane.

17. A compound represented by the formula

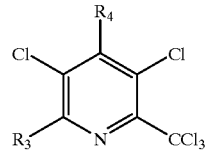

wherein one of $R_3$ or $R_4$ is Cl and the other of $R_3$ or $R_4$ is O-alkyl.

18. The compound of claim 17 wherein $R_3$ is O-alkyl and $R_4$ is Cl.

* * * * *